US010772556B2

(12) United States Patent
Ambrósio

(10) Patent No.: US 10,772,556 B2
(45) Date of Patent: Sep. 15, 2020

(54) METHOD AND SYSTEM FOR MONITORING AND TREATING HYPOGLYCEMIA

(71) Applicant: Claudio Afonso Ambrósio, Muriae (BR)

(72) Inventor: Claudio Afonso Ambrósio, Muriae (BR)

(73) Assignee: Cláudio Afonso Ambrósio, Muriae (BR)

( * ) Notice: Subject to any disclaimer, the term of this patent is extended or adjusted under 35 U.S.C. 154(b) by 225 days.

(21) Appl. No.: 14/662,011

(22) Filed: Mar. 18, 2015

(65) Prior Publication Data

US 2016/0270722 A1 Sep. 22, 2016
US 2018/0310878 A9 Nov. 1, 2018

Related U.S. Application Data

(60) Provisional application No. 62/075,719, filed on Nov. 5, 2014.

(51) Int. Cl.
*A61B 5/00* (2006.01)
*A61B 5/145* (2006.01)
*A61M 5/172* (2006.01)

(52) U.S. Cl.
CPC ........ *A61B 5/4839* (2013.01); *A61B 5/14532* (2013.01); *A61B 5/746* (2013.01); *A61M 5/1723* (2013.01)

(58) Field of Classification Search
CPC ... A61B 5/4839; A61B 5/746; A61B 5/14532; A61M 5/1723
See application file for complete search history.

(56) References Cited

U.S. PATENT DOCUMENTS

| 4,703,756 A | 11/1987 | Gough et al. |
| 5,124,314 A | 6/1992 | Cooper |
| 5,497,772 A | 3/1996 | Schulman et al. |
| 5,527,771 A | 6/1996 | Beaumont et al. |
| 5,917,414 A | 6/1999 | Oppelt et al. |
| 7,400,257 B2 | 7/2008 | Rivas |
| 8,060,576 B2 | 11/2011 | Chan et al. |
| 8,224,667 B1 * | 7/2012 | Miller .................... G06Q 50/22 705/2 |

(Continued)

FOREIGN PATENT DOCUMENTS

WO 2011/091061 7/2011

*Primary Examiner* — Navin Natnithithadha
*Assistant Examiner* — Andrey Shostak
(74) *Attorney, Agent, or Firm* — Wenderoth, Lind & Ponack, L.L.P.

(57) ABSTRACT

A system and method for monitoring a patient's blood glucose levels and communicating such levels to a patient care network is provided. More particularly, a monitor for measuring blood glucose levels may be adapted to alert the patient and preselected members of the patient care network in the event that the patient's blood glucose levels fall below a threshold amount. The monitor may be further adapted to communicate with means for automatically delivering glucose into a patient's body and means for delivering insulin into the patient's body, each means operating alone or in combination. Such a system and method may have applications in preventing symptomatic hypoglycemic episodes and providing diagnostic aid to medical professionals.

16 Claims, 4 Drawing Sheets

(56) References Cited

U.S. PATENT DOCUMENTS

| | | | |
|---|---|---|---|
| 8,368,556 B2 | 2/2013 | Sicurello et al. | |
| 8,884,751 B2 | 11/2014 | Baldocchi et al. | |
| 9,186,113 B2 | 11/2015 | Harper et al. | |
| 9,215,992 B2 | 12/2015 | Donnay et al. | |
| 9,486,571 B2 | 11/2016 | Rosinko | |
| 9,572,534 B2 | 2/2017 | Stafford | |
| 2009/0112626 A1* | 4/2009 | Talbot | G06Q 50/24 705/3 |
| 2010/0069730 A1* | 3/2010 | Bergstrom | A61B 5/0002 600/365 |
| 2011/0066044 A1 | 3/2011 | Moon et al. | |
| 2011/0124996 A1* | 5/2011 | Reinke | A61M 5/14248 600/365 |
| 2011/0313390 A1* | 12/2011 | Roy | A61M 5/158 604/500 |
| 2013/0053719 A1* | 2/2013 | Wekell | A61B 5/09 600/539 |
| 2013/0245545 A1* | 9/2013 | Arnold | A61M 5/1723 604/66 |
| 2015/0368311 A1* | 12/2015 | Haack | A61P 3/10 514/5.3 |

* cited by examiner

METHOD AND SYSTEM FOR MONITORING AND TREATING HYPOGLYCEMIA

CROSS-REFERENCE TO RELATED APPLICATIONS

Pursuant to 35 USC 119, this Application claims the benefit of Provisional Patent Application Ser. No. 62/075,719 filed on Nov. 5, 2014. The content of said application is incorporated herein by reference in its entirety.

GOVERNMENT CONTRACT

Not applicable.

STATEMENT RE. FEDERALLY SPONSORED RESEARCH/DEVELOPMENT

Not applicable.

COPYRIGHT & TRADEMARK NOTICES

A portion of the disclosure of this patent document may contain material which is subject to copyright protection. This patent document may show and/or describe matter which is or may become trade dress of the owner. The copyright and trade dress owner has no objection to the facsimile reproduction by any one of the patent document or the patent disclosure, as it appears in the Patent and Trademark Office patent files or records, but otherwise reserves all copyrights and trade dress rights whatsoever.

TECHNICAL FIELD

The disclosed subject matter relates generally to therapeutic treatment of hypoglycemia and, more particularly, to preventing symptomatic hypoglycemic episodes in, for example, diabetic patients who are being treated with insulin and/or oral hypoglycemic medications; patients with iatrogenic hypoglycemia caused by secondary conditions; patients experiencing hypoglycemia as a result of cancer; patients experiencing hypoglycemia as a result of metabolic, hormonal, and other endocrine diseases; patients having other clinical conditions that may cause hypoglycemia; or even patients with idiopathic hypoglycemia in which the root cause of the patient's condition is unknown.

The subject matter is even further related to a system and method for continuously monitoring and digitally recording blood glucose levels in order to aid future therapeutic treatment.

BACKGROUND

Hypoglycemia is a condition in which patients have abnormally low blood glucose levels. This often occurs in conjunction with glucose circulation conditions such as diabetes. Symptoms associated with abnormally low glucose levels vary and are known include, for example, nervousness and anxiety, impatience and irritability, confusion, hunger, nausea, sleepiness, blurred or impaired vision, physical weakness, fatigue, and even unconsciousness. Although about 60 to about 70 mg/dL is commonly cited as the lower range of normal glucose levels, symptoms of hypoglycemia usually do not occur until levels fall to about 50 to about 54 mg/dL (See e.g. Cryer, P E et al., *Hypoglycemia in adults: Clinical manifestations, definition, and causes*, UpToDate Inc, Apr. 26, 2013).

For treating low blood sugar, patients are often instructed to stop any insulin treatments, which continue to decrease blood sugar, and to instead consume foods, drinks, or medicinal tablets containing a prescribed amount of glucose or simple carbohydrates. Patients may alternatively be treated with Glucagon and other hormone treatments, which stimulate their own liver to release biologically stored glucose into the blood stream. For example, U.S. Pat. No. 5,527,771 to Beaumont et al. teaches providing hypoglycemic mammals with therapeutic amounts of both Calcitonin and Glucagon. U.S. Pat. No. 5,124,314 to Cooper discloses a medicinal composition for treating hypoglycemia comprising Amylin.

Thus far, the proposed solutions have been deficient. For example, treatments available fail to directly introduce glucose into a hypoglycemic patient's blood stream. As such, there may be a delay as long as many minutes between receiving treatment and alleviating symptoms of the hypoglycemic condition. For example, Glucagon must be injected into a patient's stomach and may take about six minutes to treat hypoglycemia.

Additionally, because symptoms of hypoglycemia usually present in a patient after the patient's blood glucose levels have already fallen well below healthy levels, patients are often unable to tell in advance when they are going to experience a hypoglycemic episode. Since symptoms of these episodes are generally marked by mental confusion and loss of consciousness, patients are often rendered incapable of effectively caring for themselves, by stopping insulin delivery and/or delivering glucose to their body through the prescribed methods, when the symptoms occur. This may be particularly problematic because untimely treated hypoglycemic episodes are known to have dire consequences. For example, symptoms such as dizziness and blurred and impaired vision have been known to cause traffic episodes when they occur while driving. In other instances, patients can experience hypoglycemic coma and even death if they fail to timely and effectively treat the condition.

Although various proposals have been made to solve the problem, none of those in existence combine the characteristics of the present invention. Therefore, there is a need for a method, system, and apparatus contained in a single, operative unit, which measures a patient's blood sugar, and prompts automatic or manual delivery glucose directly into a patient's body upon detecting blood sugar levels below a predetermined threshold amount.

SUMMARY

A method, system, and apparatus are provided to monitor a patient's blood glucose levels and effect timely treatment in advance of symptomatic hypoglycemic episodes. More particularly, a patient's doctors, medical specialists, emergency contacts, and other caregivers may be communicatively linked in a patient care network and may receive continuous or periodic data taken by a blood glucose monitor worn on the body of the patient. When the monitor measures blood glucose levels below a threshold amount—as may be determined based on standard medical practice or even according to a medical professional's prescription made according to the unique physiological condition of the patient—it may automatically alert the patient and one or more of the members to the patient's low blood glucose levels. Then, treatment for low blood sugar, or hypoglycemia, may occur automatically through communication with means for delivering glucose into the body of the patient. It is also contemplated that treatment may occur manually instead of automatically. In that case, a patient may be prompted to manually ingest, or caregivers may be prompted to manually provide the patient with, corrective foods, medicines, or other ingredients such as saltine crackers, orange juice, or glucose tablets. Finally, communicating blood glucose levels to various members of the patient care network, and with medical professionals in particular, may facilitate diagnosis as well as any adjustments to dosing and treatment for hypoglycemia.

For purposes of summarizing, certain aspects, advantages, and novel features have been described. It is to be understood that not all such advantages may be achieved in accordance with any one particular embodiment. Thus, the disclosed subject matter may be embodied or carried out in a manner that achieves or optimizes one advantage or group of advantages without achieving all advantages as may be taught or suggested.

In accordance with one embodiment, the system for monitoring and treating hypoglycemia comprises a monitor for measuring blood glucose. More particularly, the monitor may be any of those known to be available in the marketplace. For example, the monitor may be any of those blood glucose monitors that are configured to be worn on the body of the patient. Generally, such monitors are placed on the belly of the patient, with a sensor inserted beneath the skin, so that the sensor can contact the patient's bodily fluids and measure the blood glucose levels therein. Such monitors may be configured to continuously measure a patient's blood glucose levels. Such monitors may be configured to optionally or alternatively measure the patient's blood glucose levels on a periodic basis, such as hourly, half hourly, every ten minutes, every five minutes, or at any other increment of time as may be desired. Of course, it is also contemplated that the system for monitoring and treating hypoglycemia may be practiced using other types of blood glucose monitors and even those not yet developed. The foregoing is simply provided by way of example, and not of limitation.

Next, the monitor may be communicatively linked with one or more members comprising a patient care network. In an embodiment, the members of the patient care network may be one or more of various patient emergency contacts such as family members, friends, coworkers, and other personal acquaintances of the patient. Members of the patient care network may also be a patient's primary care physician, endocrinologist, emergency medical personnel, or even attending nurses or other caregivers.

More generally, each member of the patient care network may be a user of an electronic device in communication with the blood glucose monitor to receive information concerning the patient's hypoglycemia. To effect the communicative link with the glucose monitor, each electronic device may be any of a mobile phone, a smartphone, or a tablet computer, a pager, a personal laptop or desktop computer, or any other electronic device capable of receiving data from the glucose monitor through, for example, cellular, 3G, 4G, Bluetooth™, or Wi-Fi connectivity, or any other manner of connectivity that becomes available in the future.

In an exemplary embodiment, one or more members of the patient care network such as primary care physician, endocrinologist, nurses, and other medical personnel and caregivers may be granted access to all of the blood glucose data measured by the blood glucose monitor. Thus it is contemplated that the blood glucose monitor may communicate a patient's blood glucose trends to such members so that such members may timely plan treatments for the patient's hypoglycemia as his blood glucose levels fluctuate over a period of time. Indeed, it is even contemplated that communication from the monitor in this manner may allow such members of the patient care network to prescribe or adjust treatment as the patient's blood glucose levels fluctuate in response to various conditions such as the patient's diet and emotional state. Moreover, in an embodiment, communicated blood glucose levels may be electronically saved, either in local computing hardware or even in a remote computing cloud, for future reference. In particular, this may allow such members of the patient care network to effectively treat a patient's hypoglycemia because such members may be more readily and accurately informed of the patient's hypoglycemic condition by the automatic continuous or periodic communication of measurements taken by the blood glucose monitor over time.

In another embodiment, the blood glucose monitor may be adapted to alert the patient and/or select members of the patient care network when the patient's blood glucose levels fall below a specified threshold level. It is contemplated that this alert may effectuate timely treatment in advance of dangerous hypoglycemic symptoms. In one embodiment, the threshold level may be about 80 mg/dL. In another embodiment, the threshold blood glucose level may be about 70 mg/dL, about 60 mg/dL, about 50 mg/dL, or even about 40 mg/dL. Thus, as an example, one or more members of the patient care network who are the patient's emergency contacts may be alerted, by visual or audio alarm, page, text alert, or even phone call, that the patient has low blood sugar. This may ensure that the patient is affirmatively reminded to ingest corrective ingredients, or otherwise manually or personally given corrective ingredients for his condition even if he is unable to do so himself. Thus for example, the monitor may communicate an alarm to one or more emergency contacts so that the one or more emergency contacts may reach the patient in order to provide the patient with corrective ingredients such as saltine crackers, orange juice, or glucose tablets. This may be of particular importance when blood glucose levels reach so low that symptoms such as confusion, disorientation, and fainting occur.

In still another embodiment, corrective treatment for hypoglycemia may occur automatically. For example, the blood glucose monitor may be further communicatively linked to either or both of a means for delivering insulin into the body of the patient and a means for delivering glucose into the body of the patient. Thus, in one embodiment, the blood glucose monitor may be communicatively linked to an insulin pump, commonly available in the marketplace to treat diabetes. Continuous or periodic insulin treatments are often prescribed to suppress an excess of glucose in a diabetic patient's body, however, when a patient experiences hypoglycemia, the patient's blood glucose levels are too low, leaving the patient at risk for dangerous symptoms such as dizziness, blurred vision, confusion, and even coma. Thus, in one embodiment, when the monitor measures blood glucose levels below a threshold amount, the monitor may communicate instructions to the means for delivering insulin into the body of the patient to automatically stop delivery of the insulin.

Likewise, it is contemplated that when the monitor measures blood glucose levels below a threshold amount, the monitor may communicate instructions to the means for delivering therapeutic doses of glucose into the body of the patient to automatically begin delivery of glucose into the patient's body. Such means may be embodied as a glucose pump housed separately from, or even in combination with, an insulin pump. In any event, it is contemplated that where both a means for delivering insulin and a means for delivering glucose into the body of a patient are provided, delivery occurs alternatively. That is, when insulin is delivered into the body, glucose is not, and when glucose is delivered into the body, insulin is not.

Such a system, method, and apparatus may have applications in preventing symptomatic hypoglycemic episodes and providing diagnostic aid to medical professionals.

Thus it is an object of the invention to monitor a patient's blood glucose levels and automatically record said levels in order to aid medical professionals in planning or adjusting a course of treatment for the patient's hypoglycemia.

It is another object of the invention to communicatively link a patient's blood glucose monitor with physicians, hospitals, and/or emergency contacts defining a patient care network.

It is yet another object of the invention to alert a patient and/or one or more preselected members of the patient's patient care network to blood glucose levels below a threshold amount.

It is another object of the invention to automatically treat hypoglycemia by stopping any insulin injections when monitored blood glucose levels fall below a threshold amount.

It is still another object of the invention to automatically treat hypoglycemia by automatically injecting a patient with glucose when monitored blood glucose levels fall below a threshold amount.

It is an object of the invention to provide a device to automatically deliver alternative doses of insulin and glucose in a patient's body in response to measured blood glucose levels below predetermined threshold amounts in the event of a pancreatectomy.

One or more of the above-disclosed embodiments, in addition to certain alternatives, are provided in further detail below with reference to the attached figures. The disclosed subject matter is not, however, limited to any particular embodiment disclosed.

Although the description that follows contains many specificities, these should not be construed as limiting the scope of the embodiments, but merely as providing illustrations of some of several embodiments. Thus the scope of the embodiments should be determined by the claims that are appended and their legal equivalents rather than by the examples given. Those skilled in the art to which this invention pertains will be able to devise other forms thereof within the ambit of the appended claims.

BRIEF DESCRIPTION OF THE DRAWINGS

So that the manner in which the above recited features, advantages, and objects of the present invention are attained and can be understood in detail, a more particular description of the invention, briefly summarized above, may be had by reference to the embodiments thereof that are illustrated in the appended drawings.

It should be noted, however, that the appended drawings illustrate only typical embodiments of this invention and are therefore not to be considered limiting of its scope, for the invention may admit to other equally effective embodiments.

Figures

Figure 1:
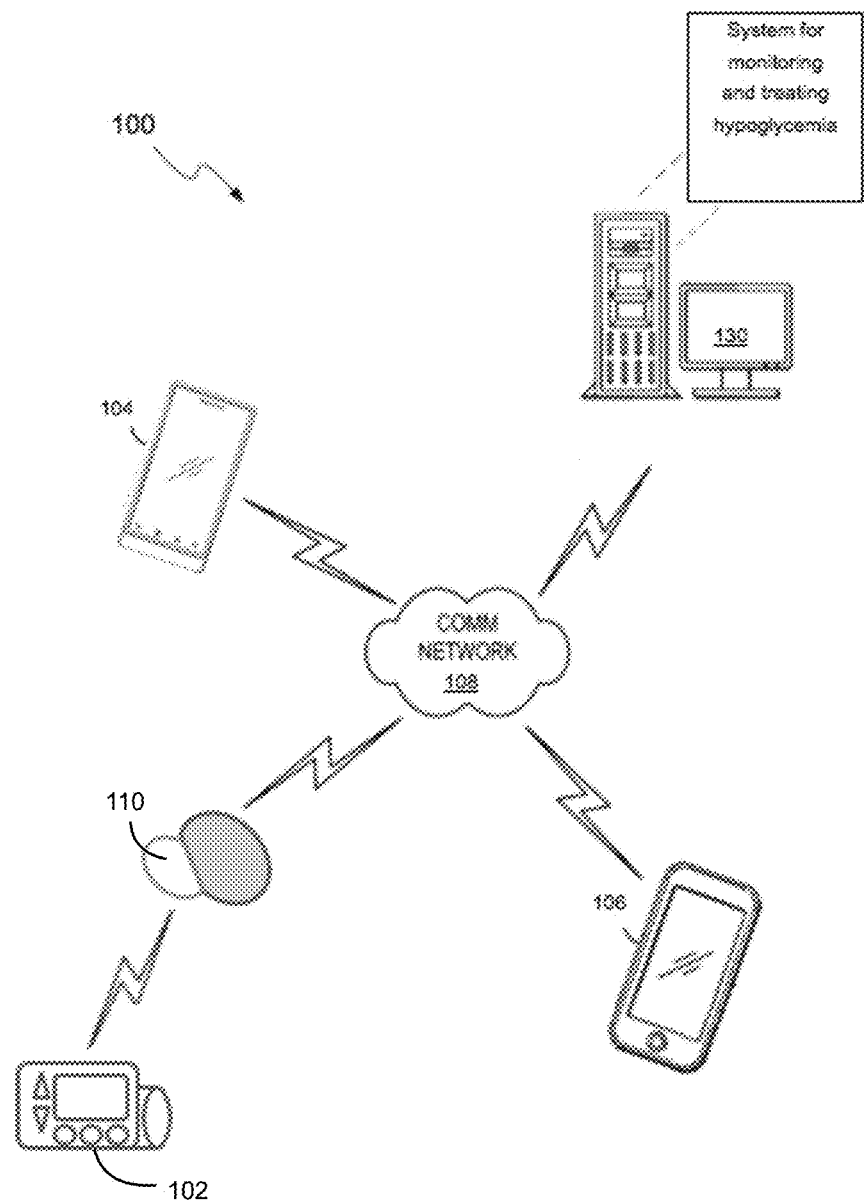

FIG. 1 depicts a block diagram of a networked environment in which an exemplary embodiment of the system for monitoring and treating hypoglycemia is implemented.

Figure 2:
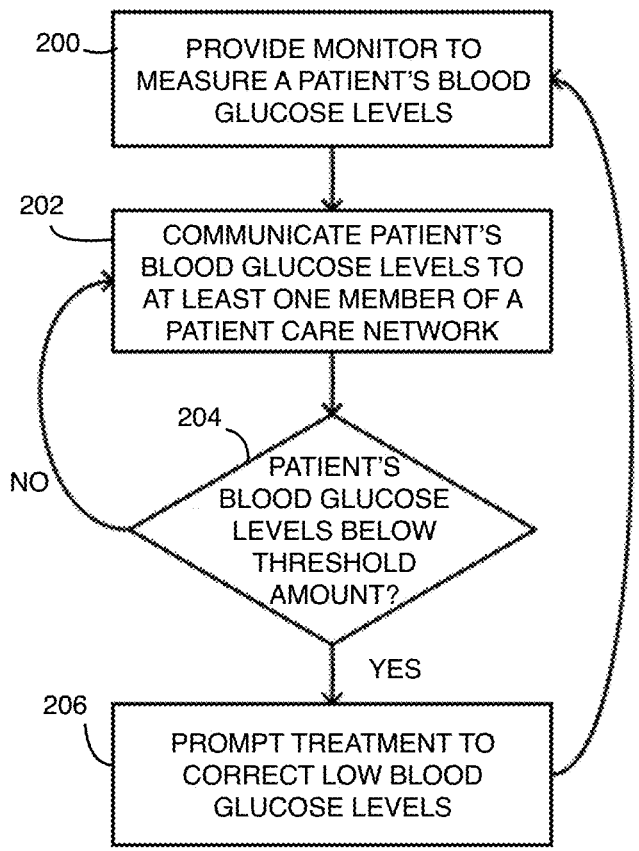

FIG. 2 is a flowchart illustrating an embodiment of the method for monitoring and treating hypoglycemia.

Figure 3:
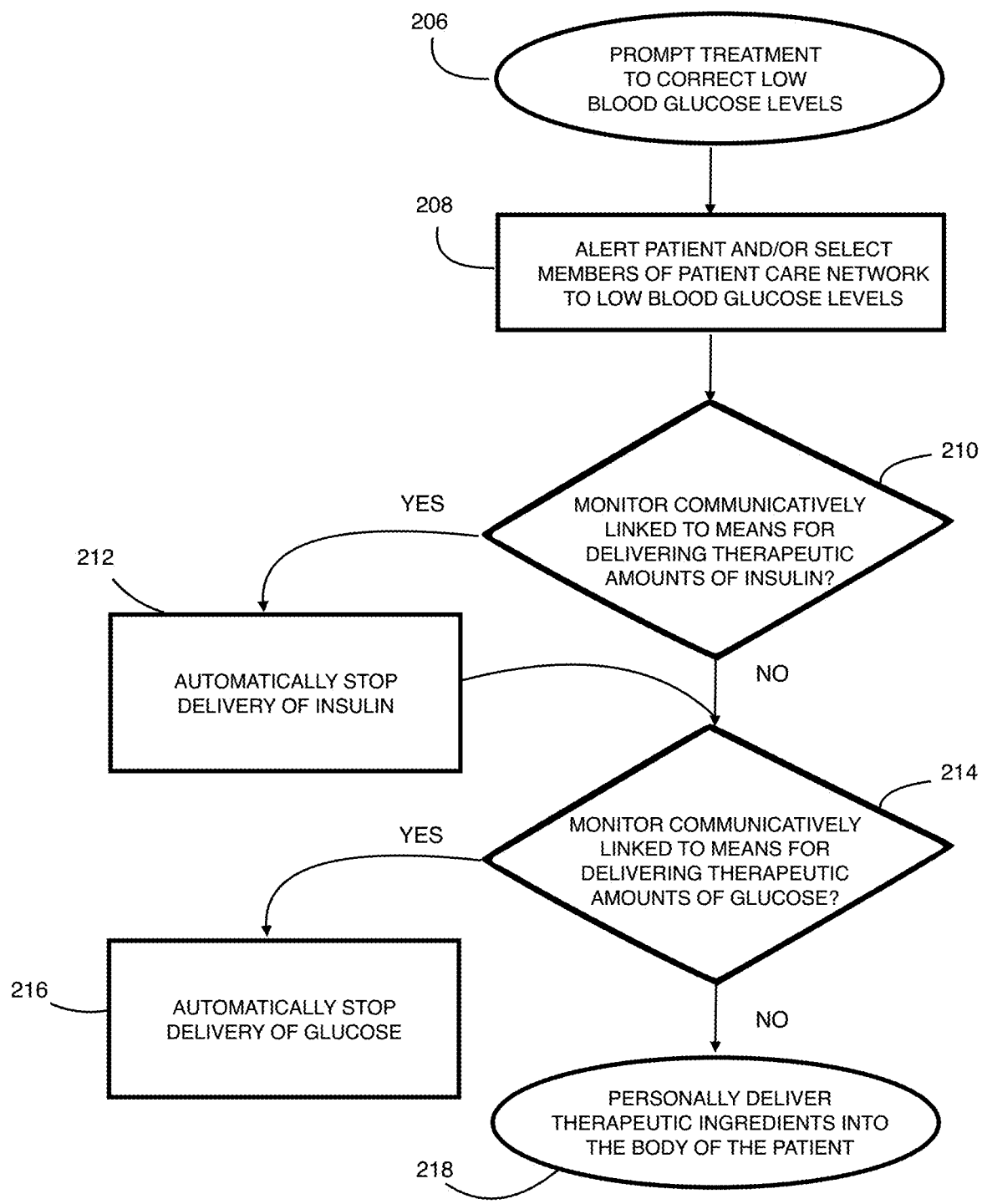

FIG. 3 is a flowchart illustrating an embodiment of a step in the method for monitoring and treating hypoglycemia.

Figure 4:
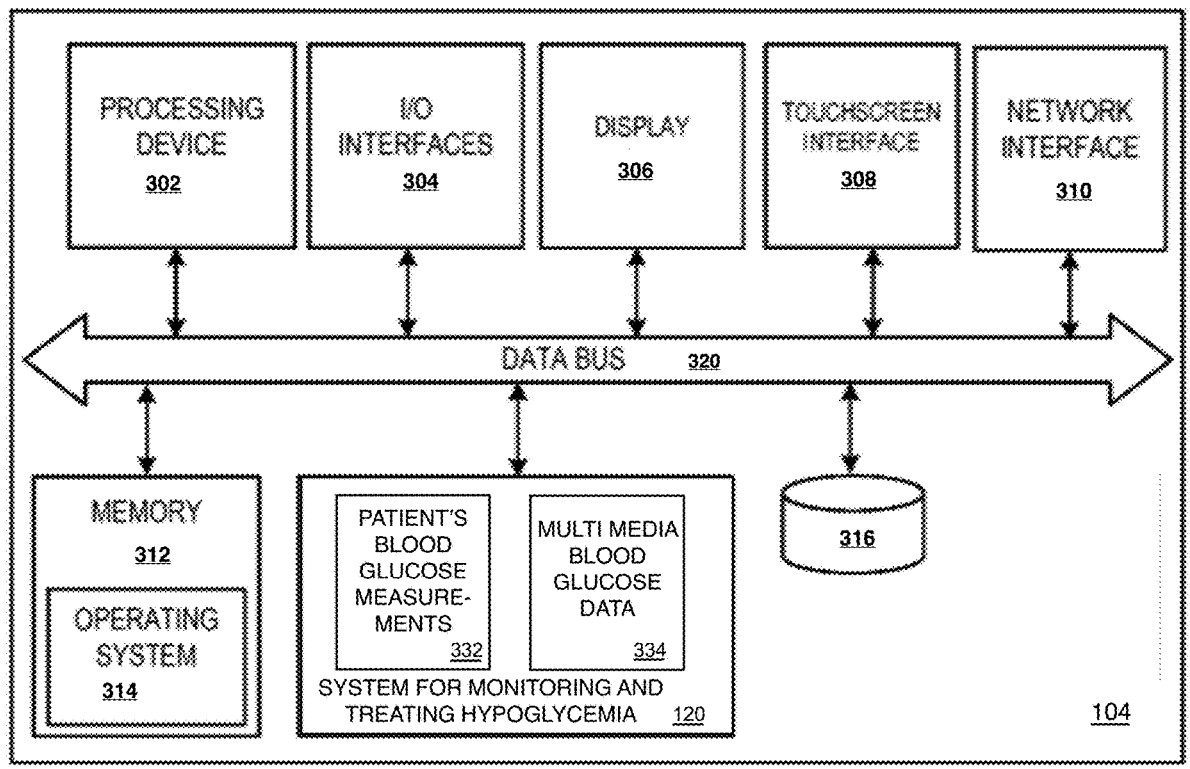

FIG. 4 depicts an exemplary embodiment of an electronic device as shown in FIG. 1.

One embodiment of the invention is implemented as a program product for use with a computer system. The program(s) of the program product defines functions of the embodiments (including the methods described herein) and can be contained on a variety of computer-readable storage media. Illustrative computer-readable storage media include, but are not limited to: (i) non-writable storage media (e.g., read-only memory devices within a computer such as CD-ROM disks readable by a CD-ROM drive) on which information is permanently stored; (ii) writable storage media (e.g., floppy disks within a diskette drive or hard-disk drive) on which alterable information is stored. Such computer-readable storage media, when carrying computer-readable instructions that direct the functions of the present invention, are embodiments of the present invention. Other media include communications media through which information is conveyed to a computer, such as through a computer or telephone network, including wireless communications networks. The latter embodiment specifically includes transmitting information to/from the Internet and other networks. Such communications media, when carrying computer-readable instructions that direct the functions of the present invention, are embodiments of the present invention. Broadly, computer-readable storage media and communications media may be referred to herein as computer-readable media.

In general, the routines executed to implement the embodiments of the invention, may be part of an operating system or a specific application, component, program, module, object, or sequence of instructions. The computer program of the present invention typically is comprised of a multitude of instructions that will be translated by the native computer into a machine-readable format and hence executable instructions. Also, programs are comprised of variables and data structures that either reside locally to the program or are found in memory or on storage devices. In addition, various programs described hereinafter may be identified based upon the application for which they are implemented in a specific embodiment of the invention. However, it should be appreciated that any particular program nomenclature that follows is used merely for convenience, and thus the invention should not be limited to use solely in any specific application identified and/or implied by such nomenclature.

For simplicity and clarity of illustration, the drawing figures illustrate the general manner of construction, and descriptions and details of well-known features and techniques may be omitted to avoid unnecessarily obscuring the invention. Additionally, elements in the drawing figures are not necessarily drawn to scale. For example, the dimensions of some of the elements in the figures may be exaggerated relative to other elements to help improve understanding of embodiments of the present invention. The same reference numerals in different figures denote the same elements.

The terms "first," "second," "third," "fourth," and the like in the description and in the claims, if any, are used for distinguishing between similar elements and not necessarily for describing a particular sequential or chronological order. It is to be understood that the terms so used are interchangeable under appropriate circumstances such that the embodiments described herein are, for example, capable of operation in sequences other than those illustrated or otherwise described herein. Furthermore, the terms "include," and "have," and any variations thereof, are intended to cover a non-exclusive inclusion, such that a process, method, system, article, device, or apparatus that comprises a list of elements is not necessarily limited to those elements, but may include other elements not expressly listed or inherent to such process, method, system, article, device, or apparatus.

The terms "couple," "coupled," "couples," "coupling," and the like should be broadly understood and refer to connecting two or more elements or signals, electrically, mechanically or otherwise. Two or more electrical elements may be electrically coupled, but not mechanically or otherwise coupled; two or more mechanical elements may be mechanically coupled, but not electrically or otherwise coupled; two or more electrical elements may be mechanically coupled, but not electrically or otherwise coupled. Coupling (whether mechanical, electrical, or otherwise) may be for any length of time, e.g., permanent or semi-permanent or only for an instant.

DETAILED DESCRIPTION

Having summarized various aspects of the present disclosure, reference will now be made in detail to that which is illustrated in the drawings. While the disclosure will be described in connection with these drawings, there is no intent to limit it to the embodiment or embodiments disclosed herein. Rather, the intent is to cover all alternatives, modifications and equivalents included within the spirit and scope of the disclosure as defined by the appended claims.

Methods and systems for monitoring and treating hypoglycemia in a patient are provided that, in some embodiments, permit one or more members of a patient care network to receive continuous or periodic data pertaining to a patient's blood glucose levels. In some embodiments, it is contemplated that the one or more members, including the patient himself, may be automatically alerted in the event that the patient's blood glucose levels fall below any threshold amounts. Moreover, embodiments are contemplated that provide automatic treatment by way of glucose injection in order to prevent or avoid symptomatic hypoglycemic episodes.

As shown in FIG. 1, system 100 may comprise a glucose monitor 102 and one or more additional electronic devices 104, 106. By way of example, the glucose monitor 102 and additional electronic devices are shown communicatively coupled via a communication network 108. Each of the electronic devices may be embodied as a mobile computing device such as, for example and without limitation, a smartphone that incorporates cellular telephone functionality. Of course, it is also contemplated that the electronic devices may be embodied as a desktop, laptop, or tablet computer. Notably, the communications network can use one or more of various communications types such as, for example and without limitation, cellular, 3G, 4G, Bluetooth™, and Wi-Fi communications.

Users of electronic devices 104 and 106 may use their devices as communicatively linked members of a patient care network that enables them to receive a patient's blood glucose data measured by the monitor 102 using their electronic devices 104 and 106 and respond, if necessary, in the event that the patient becomes hypoglycemic. In the exemplary embodiment of FIG. 1, the patient care network may be facilitated by a web-based application that is hosted by server 130. As such, server 130 facilitates interaction among a limited group of members, as may be established by the patient, the patient's primary care physician, endocrinologist, emergency contacts, and other patient caregivers. For the purpose of the exemplary embodiment presented in FIG. 1, the limited group of members comprising the patient care network includes the users of mobile devices 104 and 106.

Additionally, server 130 may implement the system for monitoring and treating hypoglycemia with the patient amongst members of the patient care network. Specifically, the server 130 implements some of the steps outlined in FIG. 2. Accordingly, pre-selected members of the patient care network may access the server 130 using their mobile devices 104 and 106 and may obtain information regarding the patient's blood glucose levels.

In order to facilitate the aforementioned functionality, various aspects of the system for monitoring and treating hypoglycemia may be performed by the glucose monitor 102 in communication with one or more of the electronic devices 104, 106. In one embodiment, an electronic device is operative to perform, at least in part, the method depicted in the flowchart of FIG. 2. Specifically, this method includes: providing a monitor to measure a patient's blood glucose levels (block 200); communicating measured blood glucose levels to at least one member of a patient care network (block 202); determining whether the patient's blood glucose levels are below a threshold amount (block 204); and, if the patient's blood glucose levels have fallen below a threshold amount, prompting treatment to correct the low blood glucose levels (block 206).

In some embodiments, certain steps in the method may be performed repeatedly. For example, a patient's blood glucose levels may be communicated to at least one member of the patient care network 202 even when blood glucose levels have not fallen below a threshold amount 204. It is contemplated that this may allow caregivers such as physicians, endocrinologists, and nursing personnel who may be members of the patient care network closely monitor a patient's glucose levels over time and even facilitate their treatment of the condition. As another example, every time the monitor determines that a patient's blood glucose levels have fallen below a threshold amount, it may prompt treatment to correct the low blood glucose levels 206.

With reference to FIG. 3, an embodiment of the prompting step 206 in FIG. 2 is illustrated as a flow chart. As illustrated, prompting treatment to correct low blood glucose levels 206 may comprise in the first instance alerting the patient to his condition 208. Such an alert may be in the form of an audio, visual, or combined audio/visual alarm housed within the monitor for measuring blood glucose levels, or elsewhere, that is triggered when the monitor measures blood glucose levels below a threshold amount. For example, the alarm may be triggered when blood glucose levels are near or below what is considered in medical practice to be normal levels. Thus, in an embodiment, the alarm may be triggered when the monitor measures blood glucose levels of about 80 mg/dL, about 70 mg/dL, about 60 mg/dL, or about 50 mg/dL. Of course, this threshold amount may be adjusted by or at the direction of the patient, a medical professional, or other caregiver. This may be especially desirable in the event that the system is employed when hypoglycemia is first detected in a patient because it is often difficult to tell immediately what blood glucose levels are normal for a particular, individualized patient. For example, some patients may become symptomatic when their blood glucose levels fall very close to typically normal levels, or about 70 mg/dL. Other patients may not become symptomatic until blood glucose levels fall much lower, or about 40 mg/dL. In any event, providing an alarm to alert In another embodiment, select members of the patient care network may also be alerted that the patient's blood glucose levels are low 208. For example, as discussed above, the monitor may be communicatively linked to members comprising the patient care network. Some of these members may be emergency contacts such as family, friends, coworkers, and other acquaintances of the patient's. As another example, some of these members may be nursing staff or caregivers in a hospital or nursing home. Such members may be alerted when the patient's blood glucose levels are low so that they may correct the patient's condition. In general, it is contemplated that such emergency contacts are chosen from those who may be able to reach the patient in the even that his hypoglycemia has rendered him incapable of effectively caring for himself. For example, it is well known that low blood sugar may cause confusion, disorientation, and even loss of consciousness. Thus, an emergency contact may be a person or caregiver or entity able to timely reach the patient in order quickly provide corrective treatment or even call emergency services for help.

Of course, such members are particularly pointed out only for the purpose of providing an example, and the nature of the relationship of each member of the patient care network to the patient is not itself intended to be limiting or dispositive.

Briefly referring to FIG. 1, in an embodiment, the monitor 102, may be further communicatively linked to either or both of a means for delivering insulin into the body of the patient and a means for delivering glucose into the body of the patient 110. This may allow corrective treatment for hypoglycemia may occur automatically. Referring also to FIG. 3, in the event that the blood glucose monitor 102 is communicatively linked to a means for delivering therapeutic amounts of insulin into the body of the patient, the monitor may instruct the means to automatically stop delivery of insulin 212. In one embodiment, means for delivering therapeutic amounts of insulin may be any insulin pump commonly available in the marketplace and known to treat diabetes. Indeed, continuous or periodic insulin treatments using pumps are often prescribed to suppress an excess of glucose in a diabetic patient's body. However, suppressing blood glucose is undesirable in the event that a patient's blood glucose levels are too low. As such, maintaining insulin treatments through hypoglycemic episodes may expedite a patient's exposure to dangerous symptoms associated with hypoglycemia, such as dizziness, blurred vision, confusion, disorientation, loss of consciousness, and even coma. Thus, in one embodiment, when the monitor measures blood glucose levels below a threshold amount, the monitor may communicate instructions to the means for delivering insulin into the body of the patient to automatically stop delivery of the insulin 212.

Likewise, the blood glucose monitor may be communicatively linked to a means for delivering therapeutic amounts of glucose into the body of the patient 214. Such means may comprise a glucose pump, similar to the insulin pumps known to exist on the market, except of course for the fact that such glucose pumps may be configured to deliver glucose into the patient's body rather than insulin. Still, any means capable of intravenously delivering therapeutic amounts of glucose into the body of the patient may be sufficient to practice the method and system of monitoring and treating hypoglycemia. As such, in an embodiment, it is contemplated that when the monitor measures blood glucose levels below a threshold amount, the monitor may communicate instructions to a means for delivering therapeutic doses of glucose into the body of the patient to automatically begin delivery of glucose into the patient's body 216. Such means may be embodied as a glucose pump housed separately from, or even in combination with, an insulin pump. In any event, it is contemplated that where both a means for delivering insulin and a means for delivering glucose into the body of a patient are provided, delivery of insulin and glucose occurs alternatively. That is, when insulin is delivered into the body, glucose is not, and when glucose is delivered into the body, insulin is not. This is because, as stated previously, insulin operates to suppress the release of glucose in the blood stream.

In still another embodiment, the method and system may be practiced independent of any means for delivering insulin and/or glucose into the body of the patient. In the event that the method and system are practiced thusly, the monitor may simply alert the patient and/or any selected members of the patient care network, via the aforementioned alarm, that the patient's blood glucose levels have fallen below a threshold amount, causing the patient and/or any selected members of the patient care network to personally deliver therapeutic ingredients into the body of the patient 218. For example, the patient may be prompted to ingest saltine crackers, a granola bar, orange juice, glucose tablets, or any other therapeutic ingredients. Of course, any selected members of the patient care network may be prompted to provide such ingredients to the patient, or even call for emergency services, as the case may be.

It should be noted that the blood glucose monitor may be configured to alert or instruct based on different threshold blood glucose levels. For example, where communicatively linked means for delivering either or both of insulin and glucose into the body of the patient, the monitor may send instructions to automatically stop delivery of insulin into the body of the patient at a higher threshold level than it will send instructions to automatically being delivery of glucose into the body of the patient. In an embodiment, the monitor may be configured to alert selected members of the patient care network only when blood glucose levels have fallen so low that it might be impossible for the patient to correct his own condition. Of course, it is also contemplated that the monitor may be configure to alert and instruct for a single threshold amount. For example, the monitor may alert the patient and selected members of the patient care network, instruct a means for delivering insulin to stop delivery of insulin, and instruct a means for delivering glucose to automatically begin delivery of glucose at the same threshold blood glucose level. It is also contemplated that any of these threshold blood glucose levels may be adjusted according to the particular physiological needs of each individual patient.

The aforementioned functions and steps can be performed by various components in various embodiments. For example, the functionality can be highly distributed across a network or less so by use of functions performed on local devices such as 102, 104 and 106.

FIG. 4 illustrates electronic device 104 shown in FIG. 1 in use by one or more of the members of the patient care network. As described, electronic device 104 may be a desktop, laptop, tablet computer, or smartphone but may also be embodied in any one of a wide variety of wired and/or wireless computing devices. As shown in FIG. 4, electronic device 104 includes a processing device (processor) 302, input/output interfaces 304, a display 306, a touchscreen interface 308 in an embodiment as a tablet computer or smartphone, a network interface 310, a memory 312, and operating system 314, and a mass storage 316, with each communicating across a local data bus 320. Additionally, mobile device 104 incorporates a system monitoring and treating hypoglycemia 100, which is depicted as including a patient's blood glucose measurements 332 as determined by embodiments of the aforementioned blood glucose monitor, and multi media blood glucose data 334, although it is contemplated that the location of information 332 and 334 could vary. For example, the information may be saved directly in hardware comprising the electronic device 104, or it may be accessible on the electronic device 104 from a remote server available through cloud computing.

The processing device 302 may include any custom made or commercially available processor, a central processing unit (CPU) or an auxiliary processor among several processors associated with the electronic device 104, a semiconductor based microprocessor (in the form of a microchip), a macroprocessor, one or more application specific integrated circuits (ASICs), a plurality of suitably configured digital logic gates, and other electrical configurations comprising discrete elements both individually and in various combinations to coordinate the overall operation of the system.

The memory 312 can include any one of a combination of volatile memory elements (e.g., random-access memory (RAM, such as DRAM, and SRAM, etc.)) and nonvolatile memory elements. The memory typically comprises native operating system 314, one or more native applications, emulation systems, or emulated applications for any of a variety of operating systems and/or emulated hardware platforms, emulated operating systems, etc. For example, the applications may include application specific software which may comprise some or all the components of the electronic device 104. In accordance with such embodiments, the components are stored in memory and executed by the processing device. Note that although depicted separately in FIG. 4, the system and method for monitoring and treating hypoglycemia 100 may be resident in memory such as memory 312.

In the event that the electronic device 104 is embodied as a tablet computer, smartphone, or even desktop or laptop computer featuring a touchscreen, touchscreen interface 308 may be configured to detect contact within the display area of the display 306 and provides such functionality as on-screen buttons, menus, keyboards, etc. that allows users to navigate user interfaces by touch. For some embodiments, the electronic device 104 may further will comprise GPS or other means to determine the location of the mobile device 104. One of ordinary skill in the art will appreciate that the memory 314 can, and typically will, comprise other components which have been omitted for purposes of brevity. Note that in the context of this disclosure, a non-transitory computer-readable medium stores one or more programs for use by or in connection with an instruction execution system, apparatus, or device. With further reference to FIG. 4, network interface device 310 comprises various components used to transmit and/or receive data over a networked environment such as depicted in FIG. 1. When such components are embodied as an application, the one or more components may be stored on a non-transitory computer-readable medium and executed by the processing device.

If embodied in software, it should be noted that each block depicted in the accompanying flowcharts represents a module, segment, or portion of code that comprises program instructions stored on a non-transitory computer readable medium to implement the specified logical function(s). In this regard, the program instructions may be embodied in the form of source code that comprises statements written in a programming language or machine code that comprises numerical instructions recognizable by a suitable execution system such as the glucose monitor 102, and electronic devices 104 and 106. The machine code may be converted from the source code, etc. If embodied in hardware, each block may represent a circuit or a number of interconnected circuits to implement the specified logical function(s). Additionally, although the flowcharts show specific orders of execution, it is to be understood that the orders of execution may differ.

CONCLUSIONS, RAMIFICATIONS, AND SCOPE

While certain embodiments of the invention have been illustrated and described, various modifications are contemplated and can be made without departing from the spirit and scope of the invention. For example, the system and method for monitoring and treating hypoglycemia may be practiced in conjunction with, or even without, either or both of an insulin pump and a glucose pump. Moreover, such pumps may be configured to operate as a singed unit, or separately from one another. Accordingly, it is intended that the invention not be limited, except as by the appended claim(s).

The teachings disclosed herein may be applied to other systems, and may not necessarily be limited to any described herein. The elements and acts of the various embodiments described above can be combined to provide further embodiments. All of the above patents and applications and other references, including any that may be listed in accompanying filing papers, are incorporated herein by reference. Aspects of the invention can be modified, if necessary, to employ the systems, functions and concepts of the various references described above to provide yet further embodiments of the invention.

Particular terminology used when describing certain features or aspects of the invention should not be taken to imply that the terminology is being refined herein to be restricted to any specific characteristics, features, or aspects of the method, system, and apparatus for monitoring and treating hypoglycemia with which that terminology is associated. In general, the terms used in the following claims should not be constructed to limit the method, system, and apparatus for monitoring and treating hypoglycemia to the specific embodiments disclosed in the specification unless the above description section explicitly define such terms. Accordingly, the actual scope encompasses not only the disclosed embodiments, but also all equivalent ways of practicing or implementing the disclosed method, system, and apparatus. The above description of embodiments of the method, system, and apparatus for monitoring and treating hypoglycemia is not intended to be exhaustive or limited to the precise form disclosed above or to a particular field of usage.

While specific embodiments of, and examples for, the method, system, and apparatus are described above for illustrative purposes, various equivalent modifications are possible for which those skilled in the relevant art will recognize.

While certain aspects of the method, system, and apparatus disclosed are presented below in particular claim forms, various aspects of the method, system, and apparatus are contemplated in any number of claim forms. Thus, the inventor reserves the right to add additional claims after filing the application to pursue such additional claim forms for other aspects of the method, system, and apparatus for monitoring and treating hypoglycemia.

What is claimed is:

1. A system for monitoring and treating hypoglycemia in a patient, the system comprising:
   a glucose pump configured to deliver therapeutic doses of glucose into the patient;
   an insulin pump configured to deliver therapeutic doses of insulin into the patient;
   a patient care network, facilitated by a web-based software application that facilitates interaction amongst a limited group of members defined by the patient care network with one another, wherein the limited group of members of the patient care network includes the patient, at least one medical professional associated with at least one first electronic device, and at least one emergency contact associated with at least one second electronic device, wherein each of the at least one first electronic device and the at least one second electronic device are configured to receive and display at least one glucose reading; and
   a monitor communicatively coupled to the glucose pump, the insulin pump, the at least one first electronic device and the at least one second electronic device via a communication network, wherein the monitor is configured to:
   measure blood glucose levels of the patient;
   continuously or periodically communicate the measured blood glucose levels to one or more of the at least one first electronic device and the at least one second electronic device of the patient care network via the communication network;
   determine whether one or more of the measured blood glucose levels are below one or more threshold amounts; and
   prompt treatment to correct low blood glucose levels of the patient in response to at least one of the measured blood glucose levels being below at least one of the one or more threshold amounts, wherein prompting treatment includes:
      alerting the patient via an alarm of the monitor in response to one of the measured blood glucose levels being below a first threshold amount;
      communicating an alert to one or more of the at least one first electronic device and the at least one second electronic device via the communication network in response to one of the measured blood glucose levels being below a second threshold amount that is lower than the first threshold amount;
      communicating instructions to the insulin pump to stop delivery of insulin into the patient via the communication network in response to one of the measured blood glucose levels being below a third threshold amount; and
      communicating instructions to the glucose pump to begin delivery of glucose into the patient via the communication network in response to one of the measured blood glucose levels being below a fourth threshold amount that is lower than the third threshold amount, wherein:
      the first threshold amount for alerting the patient via the alarm of the monitor is different from the third threshold amount for communicating the instructions to the insulin pump to stop delivery of insulin; and
      the second threshold amount for communicating the alert to the one or more of the at least one first electronic device and the at least one second electronic device is different from the fourth threshold amount for communicating the instructions to the glucose pump to begin delivery of glucose.

2. The system of claim 1, wherein the alarm of the monitor is adapted to visually and/or audibly alert the patient automatically in response to one of the measured blood glucose levels being below the first threshold amount.

3. The system of claim 1, wherein
   one of the measured blood glucose levels being below the first threshold amount or the third threshold amount indicates that the patient has a blood glucose level in a range that is below normal for the patient; and
   one of the measured blood glucose levels being below the second threshold amount or the fourth threshold amount indicates that the patient has a blood glucose level in a range at which symptoms of hypoglycemia begin to occur.

4. The system of claim 1, the insulin pump and the glucose pump being configured for alternatively delivering therapeutic doses of insulin and therapeutic doses of glucose, respectively, such that insulin and glucose are not delivered into the patient at the same time.

5. The system of claim 1, wherein the monitor is configured to continuously or periodically communicate the measured blood glucose levels to the one or more of the at least one first electronic device associated with the at least one medical professional and the at least one second electronic device associated with the at least one emergency contact via the communication network using IEEE 802.11 wireless data transfer or short range device-to-device wireless data transfer.

6. A method for monitoring and treating hypoglycemia in a patient, the method comprising:
   providing a patient care network facilitated by a web-based software application that facilitates interaction amongst a limited group of members defined by the patient care network with one another, wherein the limited group of members of the patient care network includes the patient, at least one medical professional associated with at least one first electronic device, and at least one emergency contact associated with at least one second electronic device;
   providing a glucose pump configured to deliver therapeutic doses of glucose into the patient and an insulin pump configured to deliver therapeutic doses of insulin into the patient;
   providing a monitor configured to measure blood glucose levels of the patient, wherein the monitor is communicatively coupled with the glucose pump, the insulin pump, the at least one first electronic device and the at least one second electronic device via a communication network;
   continuously or periodically communicating the measured blood glucose levels to one or more of the at least one first electronic device and the at least one second electronic device of the patient care network via the communication network;
   determining whether one or more of the measured blood glucose levels are below one or more threshold amounts; and
   prompting treatment to correct low blood glucose levels of the patient in response to at least one of the measured blood glucose levels being below at least one of the one or more threshold amounts, wherein prompting treatment includes:

alerting the patient via an alarm of the monitor in response to one of the measured blood glucose levels being below a first threshold amount;

communicating an alert to one or more of the at least one first electronic device and the at least one second electronic device via the communication network in response to one of the measured blood glucose levels being below a second threshold amount that is lower than the first threshold amount;

communicating instructions to the insulin pump to stop delivery of insulin into the patient via the communication network in response to one of the measured blood glucose levels being below a third threshold amount; and communicating instructions to the glucose pump to begin delivery of glucose into the patient via the communication network in response to one of the measured blood glucose levels being below a fourth threshold amount that is lower than the third threshold amount, wherein:

the first threshold amount for alerting the patient via the alarm of the monitor is different from the third threshold amount for communicating the instructions to the insulin pump to stop delivery of insulin; and the second threshold amount for communicating the alert to the one or more of the at least one first electronic device and the at least one second electronic device is different from the fourth threshold amount for communicating the instructions to the glucose pump to begin delivery of glucose.

7. The method of claim 6, wherein:

one of the measured blood glucose levels being below the first threshold amount or the third threshold amount indicates that the patient has a blood glucose level in a range that is below normal for the patient; and one of the measured blood glucose levels being below the second threshold amount or the fourth threshold amount indicates that the patient has a blood glucose level in a range at which symptoms of hypoglycemia begin to occur.

8. The method of claim 6, wherein the insulin pump and the glucose pump are configured for alternatively delivering therapeutic doses of insulin and therapeutic doses of glucose, respectively, such that insulin and glucose are not delivered into the patient at the same time.

9. The method of claim 6, wherein the alarm of the monitor is adapted to automatically visually and/or audibly alert the patient in response to one of the measured blood glucose levels below the first threshold amount.

10. The method of claim 6, wherein the method comprises continuously or periodically communicating the measured blood glucose levels to the one or more of the at least one first electronic device associated with the at least one medical professional and the at least one second electronic device associated with the at least one emergency contact of the patient care network via the communication network using IEEE 802.11 wireless data transfer or short range device-to-device wireless data transfer.

11. The method of claim 6, further comprising adjusting one or more of the first threshold amount, the second threshold amount, the third threshold amount, and the fourth threshold amount to be patient-specific.

12. An apparatus for monitoring and treating hypoglycemia in a patient, the apparatus comprising:

a memory storing computer-readable instructions; and a processor configured to execute the computer-readable instructions to:

provide a patient care network that facilitates interaction amongst a limited group of members defined by the patient care network with one another, wherein the limited group of members of the patient care network includes the patient, at least one medical professional associated with at least one first electronic device, and at least one emergency contact associated with at least one second electronic device;

continuously or periodically receive measured blood glucose levels of the patient from a monitor via a communication network, wherein the monitor is configured to measure blood glucose levels of the patient;

continuously, periodically, or in response to a request, communicate the measured blood glucose levels of the patient to one or more of the at least one first electronic device and the at least one second electronic device of the patient care network via the communication network;

determine whether one or more of the measured blood glucose levels are below one or more threshold amounts; and prompt treatment to correct low blood glucose levels of the patient in response to at least one of the measured blood glucose levels being below at least one of the one or more threshold amounts, wherein prompting treatment includes:

causing the monitor to alert the patient via an alarm of the monitor in response to one of the measured blood glucose levels being below a first threshold amount;

communicating an alert to one or more of the at least one first electronic device and the at least one second electronic device via the communication network in response to one of the measured blood glucose levels being below a second threshold amount that is lower than the first threshold amount;

causing an insulin pump to stop delivery of insulin into the patient in response to one of the measured blood glucose levels being below a third threshold amount; and causing a glucose pump to begin delivery of glucose into the patient in response to one of the measured blood glucose levels being below a fourth threshold amount that is lower than the third threshold amount, wherein:

the first threshold amount for causing the monitor to alert the patient via the alarm of the monitor is different from the third threshold amount for causing the insulin pump to stop delivery of insulin; and the second threshold amount for communicating the alert to the one or more of the at least one first electronic device and the at least one second electronic device is different from the fourth threshold amount for causing the glucose pump to begin delivery of glucose.

13. The apparatus of claim 12, wherein causing the monitor to alert the patient via the alarm includes causing the alarm to visually and/or audibly alert the patient automatically in response to one of the measured blood glucose levels being below the first threshold amount.

14. The apparatus of claim 12, wherein:

one of the measured blood glucose levels being below the first threshold amount or the third threshold amount indicates that the patient has a blood glucose level in a range that is below normal for the patient; and one of the measured blood glucose levels being below the second threshold amount or the fourth threshold amount indicates that the patient has a blood glucose level in a range at which symptoms of hypoglycemia begin to occur.

15. The apparatus of claim 12, wherein the processor is configured to execute the computer-readable instructions to cause the insulin pump and the glucose pump to alternatively deliver therapeutic doses of insulin and therapeutic doses of glucose, respectively, such that insulin and glucose are not delivered into the patient and the same time.

16. The apparatus of claim 12, wherein the processor is configured to execute the computer-readable instructions to:

continuously or periodically receive the measured blood glucose levels from the monitor via the communication network using IEEE 802.11 wireless data transfer or short range device-to-device wireless data transfer; and continuously, periodically, or in response to the request, communicate the measured blood glucose levels to the one or more of the at least one first electronic device associated with the at least one medical professional and the at least one second electronic device associated with the at least one emergency contact of the patient care network via the communication network using wired data transfer, cellular data transfer, IEEE 802.11 wireless data transfer, or short range device-to-device wireless data transfer.

\* \* \* \* \*